US011047778B2

(12) United States Patent
Olivier et al.

(10) Patent No.: US 11,047,778 B2
(45) Date of Patent: Jun. 29, 2021

(54) SAMPLE PREPARATION DEVICE

(71) Applicant: MERCK PATENT GMBH, Darmstadt (DE)

(72) Inventors: Stephane Olivier, Rosheim (FR); Fabrice Comini, Selestat (FR)

(73) Assignee: MERCK PATENT GMBH, Darmstadt (DE)

(*) Notice: Subject to any disclaimer, the term of this patent is extended or adjusted under 35 U.S.C. 154(b) by 424 days.

(21) Appl. No.: 15/772,425

(22) PCT Filed: Oct. 13, 2016

(86) PCT No.: PCT/EP2016/001700
§ 371 (c)(1),
(2) Date: Apr. 30, 2018

(87) PCT Pub. No.: WO2017/071795
PCT Pub. Date: May 4, 2017

(65) Prior Publication Data
US 2018/0328823 A1 Nov. 15, 2018

(30) Foreign Application Priority Data
Oct. 30, 2015 (EP) .................................. 15290279

(51) Int. Cl.
*G01N 1/40* (2006.01)
*B01L 3/00* (2006.01)
(Continued)

(52) U.S. Cl.
CPC ......... *G01N 1/4077* (2013.01); *B01D 63/087* (2013.01); *B01L 3/502* (2013.01);
(Continued)

(58) Field of Classification Search
CPC ......... G01N 1/4077; G01N 2001/4088; C12M 37/04; C12M 37/00; B01L 3/502; B01D 63/087; B01D 2313/04
See application file for complete search history.

(56) References Cited

U.S. PATENT DOCUMENTS 4,073,693 A 2/1978 Janin
6,129,828 A 10/2000 Sheldon et al.
(Continued)

FOREIGN PATENT DOCUMENTS

DE 60029623 T2 7/2007
JP 52151786 A 12/1977
(Continued)

OTHER PUBLICATIONS

Examination report in corresponding PH application 1/2018/500676 dated Nov. 5, 2020 (pp. 1-7).
(Continued)

*Primary Examiner* — Sally A Merkling
(74) *Attorney, Agent, or Firm* — Millen, White, Zelano & Branigan, PC; Ryan Pool

(57) ABSTRACT

A sample preparation device (1) comprising a first chamber (2) containing a membrane support (30) on which a membrane (9) is placed or can be placed, an inlet (20) to the first chamber (2) and an outlet (21) from the first chamber (2), at least one second chamber (3) provided with or adapted to be provided with an anaerobic generation means (23) and/or an anaerobic detection indicator, wherein the at least one second chamber (3) is connected to the first chamber (2) by a communication path (8), wherein the communication path (8) is liquid-tightly closed by a tap device (4) in a first position (A) of the tap device (4) and is adapted to be opened to allow fluid communication between the first chamber (2)
(Continued)

and the at least one second chamber (3) in that the tap device (4) is moved to a second position (B) of the tap device (4).

15 Claims, 4 Drawing Sheets

(51) Int. Cl.
  *B01D 63/08* (2006.01)
  *C12M 1/12* (2006.01)
(52) U.S. Cl.
  CPC ......... *C12M 37/04* (2013.01); *B01D 2313/04* (2013.01); *C12M 37/00* (2013.01); *G01N 2001/4088* (2013.01)

(56) References Cited

U.S. PATENT DOCUMENTS

| | | | |
|---|---|---|---|
| 6,776,294 | B2 | 8/2004 | Lemonnier |
| 10,139,322 | B2 | 11/2018 | Olivier et al. |
| 2015/0153257 | A1* | 6/2015 | Olivier ................ B01D 63/087 |
| | | | 422/534 |
| 2019/0194595 | A1 | 6/2019 | Bjork et al. |

FOREIGN PATENT DOCUMENTS

| | | | |
|---|---|---|---|
| JP | 2015529797 | A | 10/2015 |
| WO | 2013070730 | A2 | 5/2013 |
| WO | 2014005669 | A1 | 1/2014 |
| WO | 2014197831 | A1 | 12/2014 |
| WO | 15061213 | A1 | 4/2015 |
| WO | 2015096885 | A1 | 7/2015 |

OTHER PUBLICATIONS

International Search Report PCT/EP2016/001700 dated Jan. 26, 2017.
Notification of Reasons for Refusal (1st Office Action) in corresponding JP Appln. No. 2018-522131 dated Jul. 30, 2020 (pp. 1-7).
Office Action dated Apr. 9, 2021 in the corresponding Indian Examination Procedure for application No. 201837019586 (pp. 1-5).

\* cited by examiner

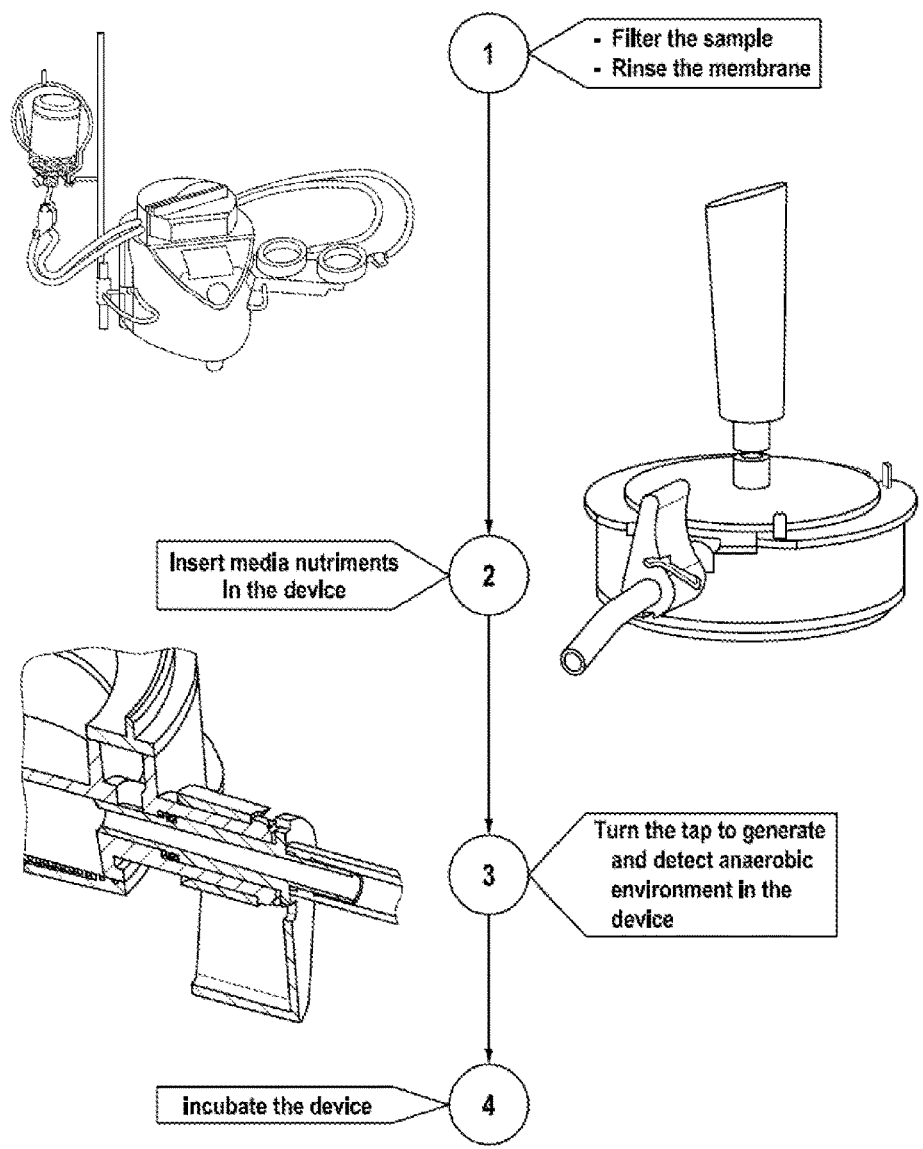
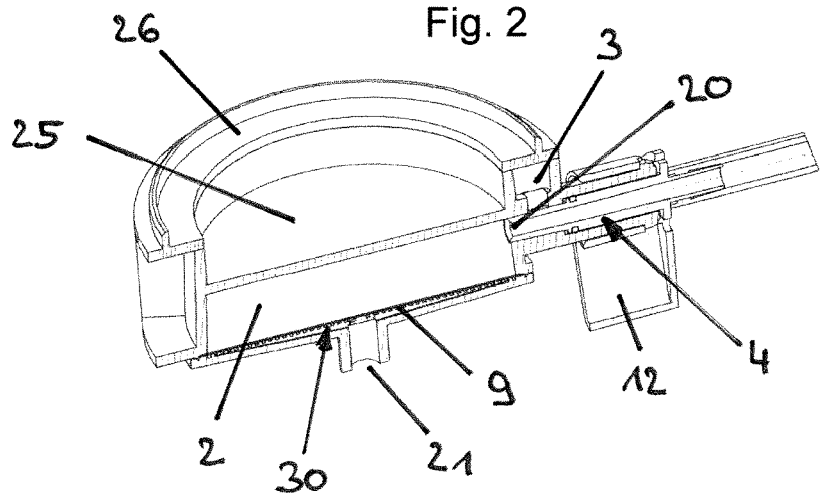

SAMPLE PREPARATION DEVICE

The invention concerns a sample preparation device preferably for sterility and bio-burden testing, for example applicable for testing purposes in connection with the control of manufacturing processes or for final product testing in the pharmaceutical, biotech, food and beverage industries.

Sterility or bio-burden testing processes require a sample preparation method that involves specific consumables, hardware and sample preparation steps and the method is known as a standardized method throughout the industry. In the growth based sterility testing the sample preparation involves promoting the growth of any micro-organisms to be detected by a direct contact of liquid nutrition media that is introduced above a calibrated membrane filter that retains the micro-organisms and by incubating the container with the filter membrane and nutrition media at a predetermined temperature. Turbidity changes of the nutrition media indicate the presence of micro-organisms. Alternately, micro-organisms can be visually detected on the membrane filter.

The equipment and sample preparation steps of the sample preparation for such sterility and bio-burden testing includes the following typical steps:

1. Pre-Wetting

The pre-wetting is used to saturate the porosity of the membrane filter with the right rinsing buffer in order to avoid or reduce the risk of molecule binding to the membrane filter, mostly in case of antibiotic sterility testing. Such a process is described, for example, in European Pharmacopoeia 5.0, 2.6.1 Sterility.

A container with the buffer solution, i.e. a bottle, is connected to sample preparation devices (filtration containers) like the one described in U.S. Pat. No. 4,036,698 A, typically with a peristaltic pump located in a fluid connection between the buffer solution container and the sample preparation devices and the buffer solution is pumped through the sample preparation devices. This step is to be repeated on each of two or more sample preparation devices for each testing task.

2. Sample Filtration

This step is used to concentrate the micro-organisms on the surface of the membrane filter in the sample preparation devices. A container, i.e. a bottle or syringe, with a sample fluid is connected with the sample preparation devices typically via the peristaltic pump. This step needs to be performed simultaneously on each of the two or more sample preparation devices with a perfect equal splitting of the sample transfer and filtering through the respective sample preparation devices.

3. Rinsing

This step is used to rinse all tubing, the internal walls of the sample preparation device or container to ascertain that all the micro-organisms are collected at the surface of the membrane filter. In this step, the porosity of the membrane filter is rinsed in order to remove any inhibitor which may delay or prevent the growth development of potential contaminants (micro-organisms). This step, too, requires to connect a container, i.e. a bottle, with a rinsing fluid to the sample preparation devices typically via the peristaltic pump and to achieve the desired fluid flow through the volume of the devices. This step, too, has to be performed on each of the two or plural sample preparation devices.

4. Growth Media Addition

This step is used to bring the right volume of nutriments (aerobic or anaerobic) into each of the sample preparation devices above the membrane filter. A nutrition media container is connected to the sample preparation devices and the right volume is measured and the sample preparation devices are closed at the end of the step. This step is to be typically performed with one of the sample preparation devices with the aerobic media and then on another sample preparation device with the anaerobic media.

5. Incubation

In this step, the two or more sample preparation devices or containers are incubated under the specific incubation conditions for optimum growth development. The incubation is performed separately for the sample preparation devices or containers with the aerobic and anaerobic media.

6. Reading

Turbidity changes or local development of colonies on the filter membranes or filaments in the fluid are detected by regular reading, either by the naked eyes or by automated optical inspection technologies, to review and detect micro-bio-growth during the predetermined incubation term.

7. Identification

In case of a positive detection of a sample a liquid is extracted from the sample preparation device or container using a syringe or the like and further analysis is subsequently performed.

In order to remove the oxygen from the device in case sample testing is to be performed for anaerobic media which require anaerobic incubation it is known to add to the sample preparation device a reducing agent that removes molecular oxygen ($O_2$) that might interfere with the growth of anaerobes in that it reacts with oxygen and reduces it to water. Various reducing agents are known for this purpose and comprise for example thioglycolate which combines with dissolved $O_2$ to deplete $O_2$ in the media, oxyrase which is a bacterial respiratory enzyme that can be put in media and it combines $O_2$ with $H^+$ to remove $O_2$ by forming $H_2O$, sodium bicarbonate and sodium borohydride which are mixed with a small amount of water to produce $CO_2$ and $H^+$, or a palladium catalyst exposed in a chamber which combines with the $O_2$ in the chamber and the $H^+$ to remove $O_2$.

The presence of oxygen in the chamber can be tested by additionally providing an anaero indicator that changes color depending on the amount of oxygen in the volume of the device or chamber.

The above-mentioned steps are typical for sterility testing and a plurality of sample preparation devices have been developed for this process.

WO 2013/070730 A2, for example, discloses a sample preparation or cell culturing device for sterility testing. The device has a housing that contains a lid having an optically clear window, a fluid distribution channel, a sample injection port fluidically connected to the fluid distribution channel, a base that comprises a porous media pad on which a filter membrane is to be placed, and a media injection port located on the bottom of the base fluidically connected to the media pad. The lid mates to the base to form a sterile seal for a first chamber and the distribution channel is disposed over the media pad. A sample fluid introduced into the fluid distribution channel through a sample injection port in the lid is distributed evenly to the media pad. The housing is provided with a separate sealed compartment that contains an oxygen scavenger sufficient to render the interior of the device anaerobic and the device has an actuator for the oxygen scavenger that is activated by over rotation of the lid causing a projection to puncture the seal on the scavenger or by a pull tab accessed through a septum located on the outside and disrupting the seal. The device may also contain an indicator of the interior oxygen content. Inlet and outlet ports of this device are preferably self-sealing and the volume between the lid and the membrane may be pressurizable to prevent excess media from pooling on top of the pad or leaking through a membrane.

It is an object of the present invention to provide a sample preparation device, preferably for sterility testing, which is further improved with respect to the efficiency and accuracy of performing the steps of the process, especially the establishing and monitoring of the incubation under anaerobic conditions.

To solve this object, the present invention provides a sample preparation device. Preferred embodiments of the sample preparation device are defined in the dependent claims.

The sample preparation device, for example for use in the sterility testing process, comprises a first chamber containing a membrane support on which a membrane is placed or can be placed, an inlet to the first chamber and an outlet from the first chamber, at least one second chamber provided with or adapted to be provided with an anaerobic generation means and/or an anaerobic detection indicator, wherein the at least one second chamber is connected to the first chamber by a communication path, wherein the communication path is liquid-tightly closed by a tap device in a first position of the tap device and is adapted to be opened to allow fluid communication between the first chamber and the at least one second chamber in that the tap device is moved to a second position of the tap device.

The sample preparation device of the invention is a closed system that contains all the structural requirements to allow in a common process as described above, the filtering/rinsing of a sample to be tested and the growth of anaerobic micro-organisms of the sample after filter concentration on a membrane by creating $O_2$ depletion in the chamber holding the membrane in a user friendly, simple and intuitive operation and in a closed unit without the risk of external contamination and without requiring additional inlet and/or outlet channels for the anaerobic generation substance.

Preferably, the tap device is arranged to be translated and/or rotated between the first and second positions.

Preferably, a seal arrangement is provided between the tap device and the communication path.

Preferably, the seal arrangement is arranged to withstand a pressure of at least 3 bar, preferably at least 5 bar in the first chamber when the tap device is in the first position.

Preferably, the seal arrangement includes mating conical seal surfaces.

Preferably, the tap device comprises a stem section movably received in a socket and an operating feature accessible to a user from outside to allow introduction of a force required to effect the movement.

Preferably, the operating feature includes a lever, preferably in the form of a flap, arranged to be operated by a user, and the stem section is arranged to be guided in the socket to perform a combined translational-rotational movement upon operation of the lever.

Preferably, a fluid channel, preferably serving as the inlet to the first chamber, extends through the stem section and has an opening at an outside port.

Preferably, the seal arrangement is arranged between the stem section and the socket.

Preferably, the mating conical seal surfaces of the seal arrangement are formed on the stem section and the socket, respectively.

Preferably, the seal arrangement comprises a further seal device, preferably made of rubber, that is provided between the stem section and the socket upstream of the communication path connecting the at least one second chamber with the first chamber.

Preferably, a connection of the communication path to the first chamber is arranged such that it is located spaced apart from a rotation center of the sample preparation device in at least one orientation of the sample preparation device and provides a continuous smooth transition for fluid from the first chamber into the communication path (8) and further into the at least one second chamber in said at least one orientation.

Preferably, a wall of the first and/or the at least one second chamber is at least partially transparent to allow visual inspection of the interior space of the respective chamber.

Preferably, at least one of the at least one second chamber is provided with a generation means in the form of a substance adapted to produce a chemical reaction, preferably a combination of an ascorbic acid and activated carbon, or with a means adapted to make a physical reaction, preferably a resistive material with a carbon layer arranged to produce heat on application of an electrical current.

Preferably, at least one of the at least one second chamber is provided with an anaerobic detection indicator in the form of a substance adapted to produce a chemical colorimetric reaction or in the form of a sensor adapted to generate and feed an electrical signal to the outside of the device.

Although the invention is described with respect to the use of the sample preparation device in a sterility testing process, the device is useful in a more general sense for processes where certain substances provided in a volume are to be processed under anaerobic conditions in a predictable, reliable, safe, sterile and repeatable manner.

The sample preparation device of the invention is compatible with existing sample preparation procedures including high pressure filtration and fluid supply using peristaltic pumps or a direct connection with a pressurized tank connected to the inlet, and vacuum filtration using a vacuum manifold or a liquid pump connected to the outlet of the device.

The method of preparing a sample for sterility testing comprises providing at least one sample preparation device according to the invention and including a membrane in the first chamber, pre-wetting the membrane, filtering the sample through the membrane, optionally rinsing the membrane, transferring the nutrition medium, thereby bringing the nutrition medium in contact with the membrane, incubating the sample preparation device in specific incubation conditions which are selected by operating the tap device and allowing fluid communication between the first chamber and the second chamber that contains the anaerobic generation means, and prior inspecting the membrane for the existence of micro-organisms, the sample preparation device may be turned over and centrifugation (with or without the application of heat) may be applied to the device to force liquid or mist droplets existing in the first chamber to go through the communication path into the one or to another second chamber and wet an indicator substance or device placed therein if needed. This can be especially advantageous in case of a high condensation level inside the device due to humidity coming from the filtration but also from a chemical reaction during anaerobic environment generation. The increased humidity created in the second chamber(s) can enhance the calorimetric reaction in the environment of the anaerobic detection sensor to achieve higher sensitivity and color contrast, for example.

BRIEF DESCRIPTION OF THE DRAWINGS

The present invention will now be described on the basis of a number of preferred embodiments using the attached drawing. In this drawing:

FIG. 2 shows a cross section perspective view of a preferred embodiment of the sample preparation device using the principle shown in FIG. 1;

FIG. 7 shows a sequence of typical steps of a method of sample preparation using the sample preparation device of the invention.

The sample preparation device of the invention and the method of preparing a sample for sterility testing using the sample preparation device will now be described below referring to the schematic principle of the device and to various specific embodiments of the principle.

FIGS. 1A to 1D show the sample preparation device 1 with its basic structural elements in a schematic representation in various stages of the process of use.

Figure 4:
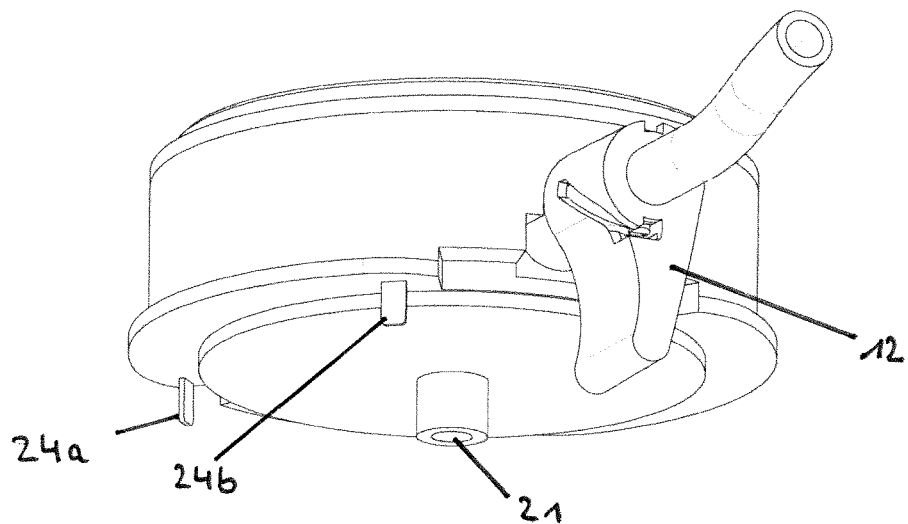
FIG. 4 shows another embodiment of a sample preparation device similar to the embodiment of FIG. 2 in perspective view.

The sample preparation device 1 of the invention comprises a first chamber 2 containing a membrane support 30 on which a membrane 9 is placed or can be placed, an inlet 20 to the first chamber 2 and an outlet 21 from the first chamber 2 (not shown in FIGS. 1A to D but in FIGS. 2 and 4). The device has at least one second chamber 3 provided with or adapted to be provided with an anaerobic generation means 23 and/or an anaerobic detection indicator (to be described later), wherein the one or more second chamber(s) 3 is/are connected to the first chamber 2 by a communication path 8.

The first chamber 2 or main cavity may be a simple cylindrical volume that is easy to rinse and has not caveats or recesses or other protrusions that could form dead legs that are not completely rinsed. The second chamber(s) 3 can be formed as one or more cavities surrounding the first chamber at the outer periphery or concentric therewith, preferably slightly raised above the level of the top wall 25 of the first chamber 2. For the various inspection purposes during and after the testing process a wall of the first 2 and/or of the at least one second chamber 3 is at least partially or fully transparent to allow visual inspection of the interior space of the respective chamber 2,3 and especially the reading and detection of the micro-organism growth on the membrane 9. In the embodiment of FIG. 2 the top recessed wall 25 of the first chamber opposite the membrane 9 could be transparent as well as the further cover 26 of the one or more second chambers 3. These covers 25, 26 can be fixedly attached to or integral with the rest of the housing or could be removable. They could also be integrally formed from a transparent material and connected with a housing body defining the first and second chambers and other functional features described later from a non-transparent or opaque plastics material.

The device of the invention has a tap device 4 formed such that the communication path 8 between the first and the one or more second chambers 2, 3 can be liquid-tightly closed when the tap device 4 is in a first position A (which would be a closed or "filtration/rinsing position") and is opened to allow fluid communication between the first chamber 2 and the one or more second chamber(s) 3 in that the tap device 4 is moved to a second position B (which would be an open or "incubation" position). The movement of the tap device 4 between the two positions can be through a translational or rotational movement of a blocking element or by a combination of the two types of movement.

A seal arrangement 15 is provided between the tap device 4 and the communication path 8 that is preferably arranged to withstand a pressure of at least 3 bar, preferably of at least 5 bar in the first chamber 2 when the tap device 4 is in the first position A. This allows filtration/rinsing of the first chamber and its membrane under elevated pressure to avoid or reduce the risk of trapping micro-organisms in channels or dead legs while avoiding or reducing the risk of ingress of fluid and wetting of anaerobic generation material in the second chamber(s) 3, i.e. the second chamber(s) 3 can be watertight during filtration even under pressurized conditions.

To withstand the increased pressure level in the first chamber 2 the seal arrangement 15 preferably includes mating conical seal surfaces 15a, 15b at an interface of a sealing element in the connection path 8. Where the mating conical seal surfaces 15a, 15b at the interface are formed with sufficient precision, the seal will be able to withstand the pressures without the need to provide further dedicated sealing material like rubber etc. at the interface. The axial length of the mating conical surfaces is determined based on the rated pressure it has to withstand. Also, the material of the surfaces also has an influence on the frictional resistance that can be created.

Figure 5:
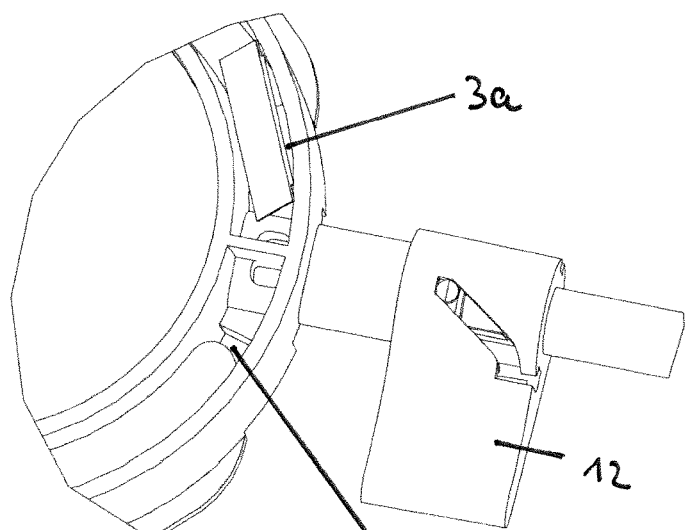
FIG. 5 shows details in cross section perspective view of the tap device and of the second chamber in the sample preparation device of FIG. 2.

In a preferred embodiment as shown in the various FIGS. the tap device 4 comprises a stem section 10 movably received in a socket 11 formed in the housing of the device, and an operating feature 12 accessible to a user from outside to allow introduction of a force required to effect the movement of the stem section 10 relative to the socket 11, i.e. to overcome the frictional force at the mating conical seal surfaces. As shown for example in FIGS. 2, 4 and 5 the operating feature 12 may include a lever, preferably in the form of a flap or lug, arranged to be operated by a thumb of the user, and the stem section 10 is arranged to be guided in the socket 11 to perform a combined translational-rotational movement upon operation of the lever. The typical means for producing such a movement are shown in FIGS. 4 and 5 and include an inclined groove or cam on the lever and a pin fixed to the stem section 10 and riding in the groove or along the cam so that the turning of the groove or cam with the operation of the lever (that is prevented itself from axial movement) forces the pin and with it the stem section to perform an axial movement defined by the inclination of the groove/cam. The elements of the groove/cam and pin can of course be exchanged between the stem and the lever.

In the shown arrangement the sealing surface 15*b* of the seal arrangement 15 is formed on the outer circumference at the forward end portion (left side in FIGS. 2 and 3A) of the stem section 10 and the mating conical seal surface 15*a* is at the socket 11, i.e. at the wall section of the wall separating the first chamber and the second chamber up to the inlet to the second chamber. A particular advantage of the device in terms of simplification is achieved where a fluid channel 16 that serves as or forms part of the inlet 20 to the first chamber 2 extends through the stem section 10 and has an opening at an outside port 13. In this way the pre-wetting (if needed), the sample introduction and the rinsing can be effected through the same channel. The port 13 may be provided with a form to allow tight insertion into a tube, hose or conduit of the sample testing setup. It may also be arranged to cooperate with common connectors.

Figure 3A:
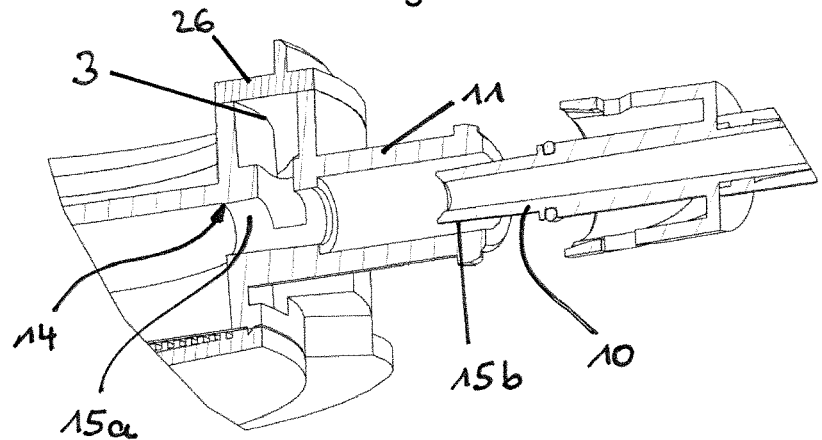
FIGS. 3A to 3C show details in cross section perspective view of the tap device in the sample preparation device of FIG. 2 in operation.
Figure 3B:
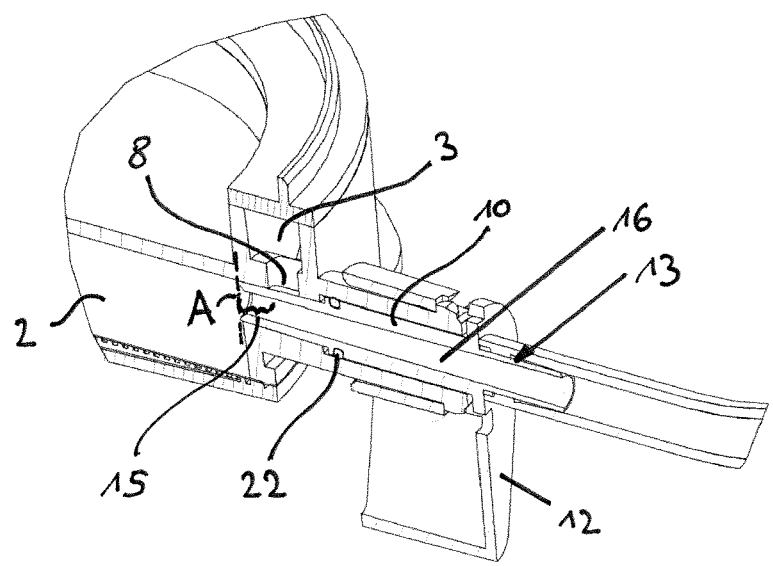
Figure 3C:
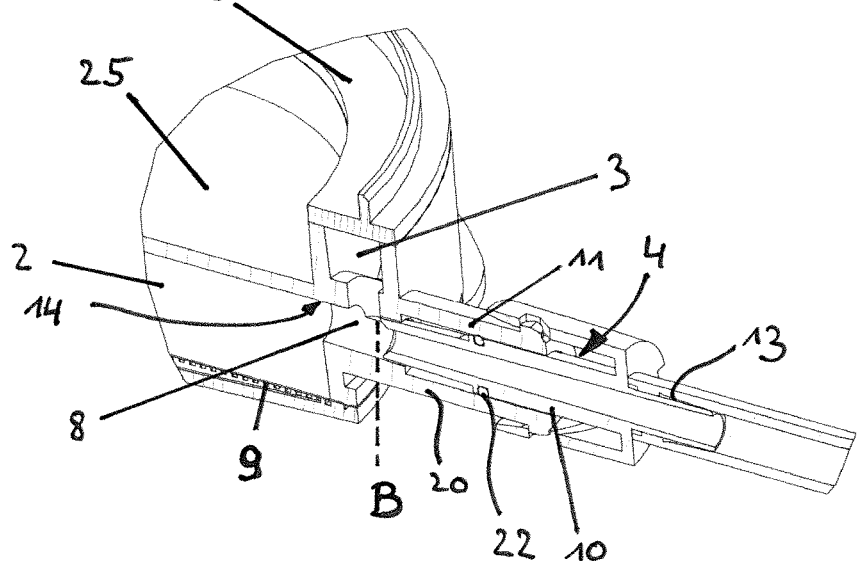

As shown in FIGS. 3A, 3B and 3C the seal arrangement 15 may comprise a further seal device 22, preferably made of rubber and in the form of one or more O-ring(s) or a gland seal, that is provided between the stem section 10 and the socket 11 upstream of the communication path 8 connecting the at least one second chamber 3 with the first chamber 2. At this position the further seal device 22 does not have to support any pressure in the closed position of the tap device 4 (because the conical seal surfaces upstream create a sufficient seal of pressure existing in the first chamber) and only a relatively small pressure differential in the open position B of the tap device 4 where the anaerobic incubation takes place. Its main purpose is thus to protect the second chamber(s) and the communication path 8 from external contamination in both positions of the tap device 4.

Figure 1A:
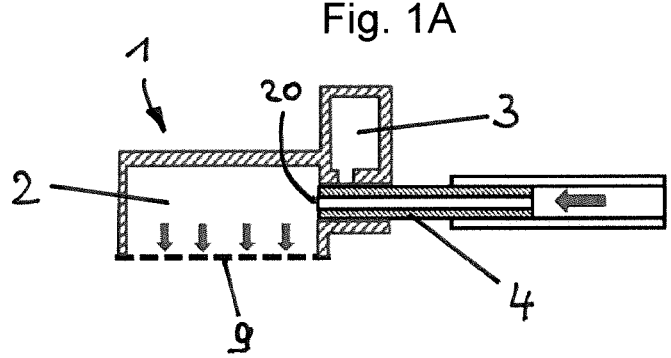
FIG. 1A to 1D show a schematic representation of a sample preparation device of the present invention in various stages of the process of use to explain the structure and functional principle.
Figure 1B:
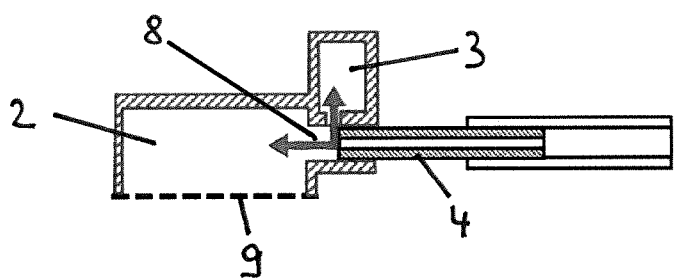
Figure 1C:
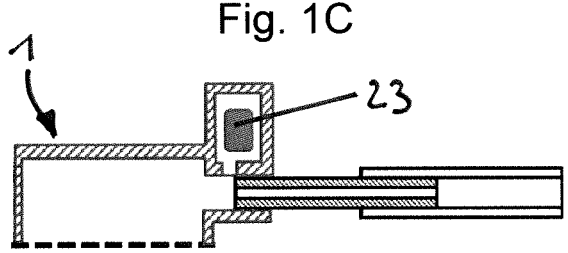
Figure 1D:
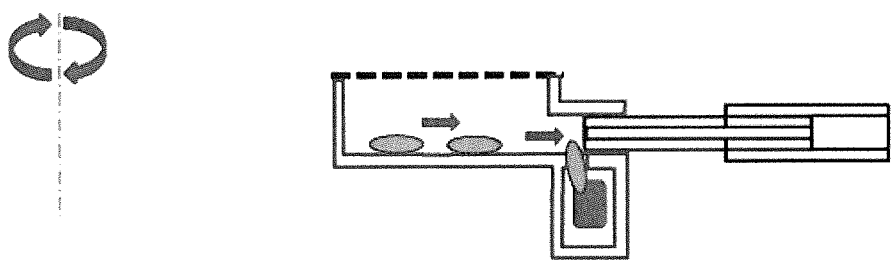

As shown for example in FIGS. 2 and 3A and 1D a connection or transition 14 of the communication path 8 to the first chamber 1 is arranged such that it is located spaced apart from a (fictive) rotation center of the sample preparation device 1 in a centrifuge in at least one orientation of the sample preparation device 1 (top down in the FIG. 1D) and such that it provides a continuous smooth transition for fluid from the first chamber 2 into the communication path 8 and further along the conical seal surface 15*a* into the inlet of the at least one second chamber 3, which inlet is, in such an orientation of the device, at the same level or below the surface where the droplets stand. In the embodiment shown in the drawing the inner surface of the cover 25 of the first chamber 2 is flush with the communication path 8. Thus, if a centrifugation (with or without the application of heat) is applied to the device this will force liquid or mist droplets existing in the first chamber to go to the outer circumference of the first chamber and into and through the communication path 8 into the one or more second chamber(s) where it may wet an indicator substance or a sensor device placed therein. At least one of the one or more second chamber(s) 3 is preferably provided with (pre-filled with or dimensioned for receiving it later) a generation means in the form of a substance adapted to produce a chemical reaction to create a specific atmosphere for specimen incubation, for example a combination of an ascorbic acid and activated carbon, or with a means adapted to make a physical reaction, preferably a resistive material with a carbon layer arranged to produce heat on application of an electrical current.

Other substances adapted to produce the desired atmosphere, preferably an anaerobic atmosphere in the first chamber may be used as well. Such anaerobic generation substances are known per se and they may be packed in a bag or sachet or provided as loose substance in the chamber. The substance becomes activated by exposure to air and the substance rapidly reduces the oxygen concentration within the respective volume. At the same time, inorganic carbonate produces carbon dioxide and this produces the atmosphere suitable to support the primary isolation and cultivation of anaerobic, micro-aerophilic or capnophilic bacteria by use of gas-generating substances of the respective type inside the volume of the second chamber(s). The exposure to air is made and the substance is activated when the tap device 4 opens the communication path 8 by moving to the second position B as shown in FIG. 3C.

Further, at least one of the at least one second chamber 3 may be provided with an anaerobic detection indicator in the form of a substance adapted to produce a chemical colorimetric reaction (reversible or not) or in the form of a sensor adapted to generate and feed an electrical signal to the outside of the device. In FIG. 4 electrical contacts 24*a,b* protruding from the bottom side of the device are shown as examples of contact means for such a sensor arrangement. Other contact means, i.e. in the form of standard-miniaturized plugs and sockets for electrical connections or even wireless solutions for transmitting signals from the second chamber(s) to the outside may be applied.

If an electrical power or current is required to operate any of the above mentioned devices this could be supplied into the device through a standard electrical connector, i.e. together with leads for the signal output, or by induction.

The anaerobic detection indicator and the anaerobic generation means may be provided in the same second chamber or may be provided in two different second chambers 3*a*, 3*b* that are arranged so as to be simultaneously communicated with the first chamber through the communication path 8 when the tap device is in the second position (see FIG. 5). The inlets to the chambers may be different such that the liquid droplets during centrifugation as described above enter only into one of the chambers that requires the additional humidity for detection purposes.

The second chamber(s) may also hold other substances like growth or nutrition media.

Using the sample preparation device of FIGS. 4 and 7 in the sterility testing process described above includes pre-wetting of the membrane 9 on the membrane support 30 through the inlet 16, 20 and the outlet 21 while the tap device 4 is in the first (or closed) starting position A as shown in FIGS. 1A and 3B. In the second step, the sample fluid is transferred to the first chamber 2 through the same inlet 16, 20 outlet 21 to filter the sample to concentrate the microorganisms on the surface of the membrane 9. Thereafter, the rinsing step is performed, through the inlet 16, 20 and the outlet 21 like in the prior art while the tap device 4 remains in the starting position.

Following that the step of adding the growth or nutrition media is performed and the device for this purpose may be turned over so that the nutrition media is introduced through the outlet 21 (see FIG. 7). Then, if needed for the sample testing, the generation of the anaerobic atmosphere is performed in that the tap device 4 is actively moved to the second (or open) position B as shown in FIGS. 1B and 3C. This movement opens the communication path 8 and allows for fluid exchange between the second chamber(s) 3 and the first chamber 2 through the communication path 8. The communication established between the first chamber that will serve as the incubation chamber and the anaerobic generation substance in the second chamber activates the substance to produce the specific atmosphere for specimen incubation. The open communication path 8 allows the specific atmosphere to extend into the first chamber 2 or incubation chamber and get in contact with the specimens on the membrane 9.

The membrane 9 in the first chamber 2 can be supported by a mesh structure (not shown) provided on the upper surface of the bottom wall of the housing to limit the membrane deformation and avoid local stress which could damage the membrane and allow filtered sample to be drained to the outlet 21 (outlet port). The outlet 21 may be closed if needed by a plug or it may be provided with a valve (not shown). Subsequently, the sample preparation device can be subjected to the further handling including incubation of the devices according to the aerobic or anaerobic development in different temperature environments and the typical reading and/or identification steps.

Although the device is described and shown with a single inlet 20 and a single outlet 21 to/from the first chamber 2, it may be optionally provided with an additional inlet or port adapted to be connected to external tubing if needed.

Although the cover 25 of the first chamber 2 is shown as an integral part of the housing, it can be fixedly or removably attached in the form of a lid. The cover or lid is, as mentioned above, preferably transparent to allow inspection of the incubation volume or membrane of the first chamber, either by the naked eye or by using optical automatic detection devices. The cover 25 if formed as a removable lid would allow addition of rinsing and/or sample fluids to the first chamber of the device through the open top of the first chamber serving as the inlet.

Figure 6:
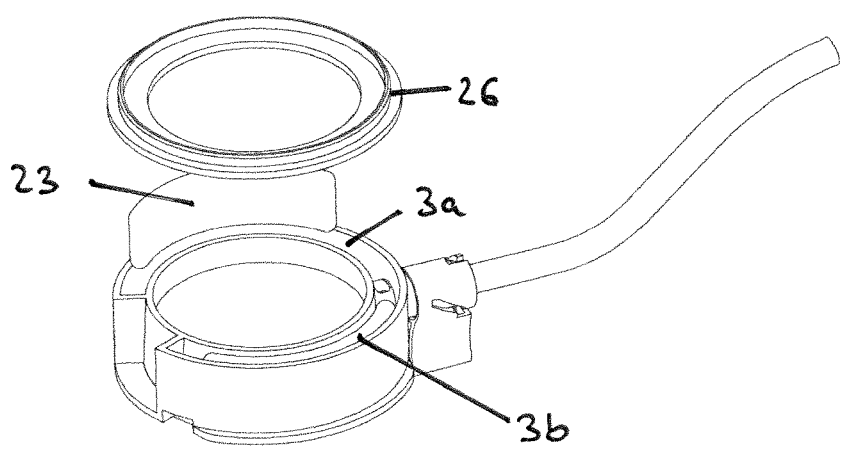
FIG. 6 shows a modification of the sample preparation device of FIG. 2 with a cover removed and with two second chambers.

Although not shown in the drawing the sample preparation device of the embodiment may be formed in a manner that the first and second chambers are not concentrically arranged as in FIG. 6 but are laterally arranged but nevertheless integrally connected in the device. The second chamber can be integrated with the first chamber but can also be removably connected therewith. This allows easy and modular manufacturing of the sample preparation device in that the second chamber including the desired nutrition media or the anaerobic generation substance is selectively attached to the first chamber. This concept reduces the number of components necessary to produce sample preparation devices for different testing applications. The connection of the first chamber and of the second chamber needs to establish communication of the inlet of the second chamber(s) with the communication path adapted to be opened/closed by the tap device.

Although not shown in the drawing the sample preparation device may be included as part of a sample preparation set comprising two sample preparation devices of the type shown in the various figures and a tubing set designed to connect the inlets of the sample preparation devices with a common vented needle or sampling port for distributing a fluid to the sample preparation devices in precise aliquots. The two sample preparation devices in the set include one for anaerobic conditions and including consequently the anaerobic generation substance in the second chamber while the other one is for aerobic conditions and consequently does not need to include the anaerobic generation substance (it may of course be the same as the other one but provided with a measure that the tap device cannot be operated). The tubing set can be designed for the respective application and there could be more than two of the sample preparation devices depending on the need. The sample preparation devices could be loaded with the same or with different nutrition media/anaerobic generation substances in the second chamber(s). Any caps needed to plug the inlet 16, 20 (preferably at the port 13) and the outlet 21 are also pre-arranged in a packaging of the set. Further functional elements of a testing equipment including tubing, clamps, needles, etc., can be included in the set. The entire package can be in a sterilized blister to avoid contamination of pre-sterilized content.

The use of the set and the introduction of the rinsing or sample fluids through the inlet port and out from the outlet port can be performed as described in connection with the prior art by using external pumps like peristaltic pumps, pressurized tanks or syringes at the inlet or vacuum devices at the outlet. The incubation also can be performed as in the prior art and the circumstances depend on the germs or bacteria to be detected because they have different and specific growth conditions. Likewise, the growth or nutriment media provided in the sample preparation device are specific to the panel of germs or bacteria to be detected and to the environmental conditions and incubation temperature conditions. Since some micro-organisms require aerobic environments while others require anaerobic conditions to grow, the two different sample preparation devices are provided, one having the anaerobic generation powder or sachet provided in the third volume of the second chamber and one having no such substance, e.g. having an empty third volume containing atmospheric gas with oxygen.

The sample preparation device of the invention is compatible with laboratory equipment including pumps, pressurized tanks or vacuum systems for performing the preparatory steps of rinsing and sample filtration. It is also compatible with current incubation and identification protocols. Lastly, the sample preparation device facilitates the handling of waste as it reduces the number of separate and independent containers used in the entire sterility testing process.

The invention claimed is:

1. A sample preparation device (1) comprising
a first chamber (2) containing a membrane support (30) on which a membrane (9) is placed or can be placed;
an inlet (20) to the first chamber (2) and an outlet (21) from the first chamber (2);
at least one second chamber (3) provided with or adapted to be provided with an anaerobic generation substance (23) and/or an anaerobic detection indicator, wherein the at least one second chamber (3) is connected to the first chamber (2) by a communication path (8),
wherein the communication path (8) includes a tap device (4) which is suitable to provide a liquid tight seal in a first position (A) of the tap device (4) and is suitable to be opened to allow fluid communication between the first chamber (2) and the at least one second chamber (3) when the tap device (4) is in a second position (B) of the tap device (4), and
wherein the tap device (4) comprises a stem section (10) movably received in a socket (11) and an operating feature (12) accessible to a user from outside to allow introduction of a force required to effect the movement of the stem section relative to the socket.

2. The sample preparation device (1) according to claim 1, wherein the tap device (4) is arranged to be translated and/or rotated between the first and second positions (A,B).

3. The sample preparation device (1) according to claim 1, wherein a seal arrangement (15) is provided between the tap device (4) and the communication path (8).

4. The sample preparation device (1) according to claim 3, wherein the seal arrangement (15) is arranged to withstand a pressure of at least 3 bar, preferably at least 5 bar in the first chamber (2) when the tap device (4) is in the first position (A).

5. The sample preparation device (1) according to claim 3, wherein the seal arrangement (15) includes mating conical seal surfaces.

6. The sample preparation device (1) according to claim 1, wherein the operating feature (12) includes a lever, preferably in the form of a flap, arranged to be operated by a user, and the stem section (10) is arranged to be guided in the socket (11) to perform a combined translational-rotational movement upon operation of the lever.

7. The sample preparation device (1) according to claim 1, wherein a fluid channel (16), preferably serving as the inlet (20) to the first chamber (2), extends through the stem section (10) and has an opening at an outside port (13).

8. The sample preparation device (1) according to claim 1 wherein a seal arrangement (15) is provided between the tap device (4) and the communication path (8) and, wherein the seal arrangement (15) is arranged between the stem section (10) and the socket (11).

9. The sample preparation device (1) according to claim 8 wherein the seal arrangement (15) includes mating conical seal features, and wherein the mating conical seal surfaces of the seal arrangement (15) are formed on the stem section (10) and the socket (11), respectively.

10. The sample preparation device (1) according to claim 9, wherein the seal arrangement (15) comprises a further seal device (22), preferably made of rubber, that is provided between the stem section (10) and the socket (11) upstream of the communication path (8) connecting the at least one second chamber (3) with the first chamber (2).

11. The sample preparation device (1) according to claim 1, wherein a connection (14) of the communication path (8) to the first chamber (1) is arranged such that it is located spaced apart from a rotation center of the sample preparation device (1) in at least one orientation of the sample preparation device (1) and provides a continuous smooth transition for fluid from the first chamber (2) into the communication path (8) and further into the at least one second chamber (3) in said at least one orientation.

12. The sample preparation device (1) according to claim 1, wherein a wall of the first (2) and/or the at least one second chamber (3) is at least partially transparent to allow visual inspection of the interior space of the respective chamber (2,3).

13. The sample preparation device (1) according to claim 1, wherein at least one of the at least one second chamber (3) is provided with a generation means in the form of a substance adapted to produce a chemical reaction, preferably a combination of an ascorbic acid and activated carbon, or with a means adapted to make a physical reaction, preferably a resistive material with a carbon layer arranged to produce heat on application of an electrical current.

14. The sample preparation device (1) according to claim 1, wherein at least one of the at least one second chamber (3) is provided with an anaerobic detection indicator in the form of a substance adapted to produce a chemical colorimetric reaction or in the form of a sensor adapted to generate and feed an electrical signal to the outside of the device.

15. A sample preparation set comprising:
  two or more sample preparation devices (1) according to claim 1, and
  a tubing set designed to connect the inlets (20) of the sample preparation devices (1) with a common connector for distributing a fluid to the sample preparation devices (1).

* * * * *